US012735521B2

(12) United States Patent
Moszner et al.

(10) Patent No.: US 12,735,521 B2
(45) Date of Patent: Sep. 15, 2026

(54) SULFATE-CONTAINING OR PHOSPHATE-CONTAINING, SELF-ADHESIVE DENTAL COMPOSITE CEMENT WITH GOOD TRANSPARENCY

(71) Applicant: Ivoclar Vivadent AG, Schaan (LI)

(72) Inventors: Norbert Moszner, Triesen (LI); Alexandros Gianasmidis, Balgach (CH); Delphine Catel, Rans (CH); Yohann Catel, Rans (CH); Andy Brot, Balzers (LI); Tim Haldner, Mauren (LI); Thorsten Bock, Feldkirch (AT); Barbara Grabenbauer, Rebstein (CN)

(73) Assignee: Ivoclar Vivadent AG, Schaan (LI)

( * ) Notice: Subject to any disclaimer, the term of this patent is extended or adjusted under 35 U.S.C. 154(b) by 907 days.

(21) Appl. No.: 18/147,690

(22) Filed: Dec. 28, 2022

(65) Prior Publication Data

US 2023/0203224 A1 Jun. 29, 2023

(30) Foreign Application Priority Data

Dec. 29, 2021 (EP) .................................... 21218209

(51) Int. Cl.

| | |
|---|---|
| ***C08F 222/38*** | (2006.01) |
| ***A61K 6/30*** | (2020.01) |
| ***A61K 6/73*** | (2020.01) |
| ***A61K 6/74*** | (2020.01) |
| ***A61K 6/77*** | (2020.01) |
| ***A61K 6/887*** | (2020.01) |
| ***C08K 3/30*** | (2006.01) |
| ***C08K 3/36*** | (2006.01) |
| ***C08K 3/40*** | (2006.01) |
| ***C08K 5/13*** | (2006.01) |
| ***C08K 13/04*** | (2006.01) |

(52) U.S. Cl.

CPC ............ *C08F 222/385* (2013.01); *A61K 6/30* (2020.01); *A61K 6/73* (2020.01); *A61K 6/74* (2020.01); *A61K 6/77* (2020.01); *A61K 6/887* (2020.01); *C08K 13/04* (2013.01); *C08F 2800/20* (2013.01); *C08K 2003/3054* (2013.01); *C08K 3/36* (2013.01); *C08K 3/40* (2013.01); *C08K 5/13* (2013.01); *C08K 2201/014* (2013.01)

(58) Field of Classification Search

CPC .... C08F 222/385; C08F 2800/20; A61K 6/30; A61K 6/73; A61K 6/74; A61K 6/77; A61K 6/887; A61K 6/61; A61K 6/62; A61K 6/889; A61K 6/15; A61K 6/71; A61K 6/76; C08K 13/04; C08K 3/36; C08K 3/40; C08K 5/13; C08K 2003/3054; C08K 2201/014

See application file for complete search history.

(56) References Cited

U.S. PATENT DOCUMENTS

| | | | | |
|---|---|---|---|---|
| 11,357,709 | B2 | 6/2022 | Moszner et al. | |
| 2002/0082317 | A1* | 6/2002 | Lyons ...................... | A61K 6/69 523/116 |
| 2007/0040151 | A1 | 2/2007 | Utterodt et al. | |
| 2020/0253837 | A1* | 8/2020 | Moszner ............... | C07C 409/12 |

FOREIGN PATENT DOCUMENTS

| | | | |
|---|---|---|---|
| DE | 10021605 | A1 | 11/2001 |
| EP | 2103296 | A1 | 9/2009 |
| EP | 3884921 | A1 | 9/2021 |
| EP | 4094748 | A1 | 11/2022 |
| JP | 2002047118 | A | 2/2002 |

* cited by examiner

*Primary Examiner* — Jessica M Roswell

(74) *Attorney, Agent, or Firm* — Ann M. Knab; Thad McMurray

(57) ABSTRACT

A radical polymerizable composition having at least one acidic radical polymerizable monomer, at least one fluoroaluminosilicate glass filler and/or radiopaque glass filler, and at least one water-soluble sulfate and/or phosphate.

14 Claims, 1 Drawing Sheet

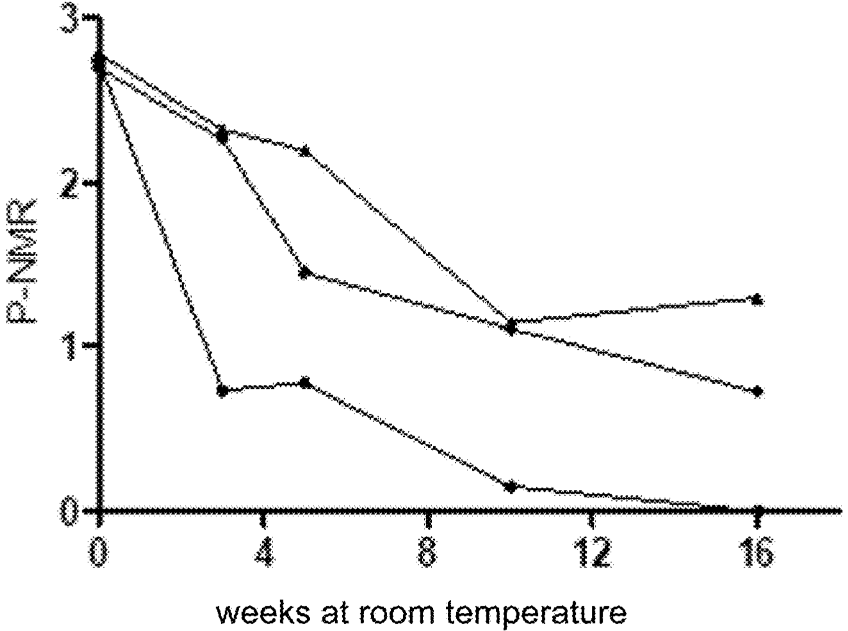
Storage stability of composites C-1 (●: without $(NH_4)_2SO_4$), C-2 (▲:1.41 wt.% $(NH_4)_2SO_4$), and C-3 (◆:0.456 wt.% $(NH_4)_2SO_4$), studied by NMR spectroscopy.

SULFATE-CONTAINING OR PHOSPHATE-CONTAINING, SELF-ADHESIVE DENTAL COMPOSITE CEMENT WITH GOOD TRANSPARENCY

CROSS-REFERENCE TO RELATED APPLICATIONS

This application claims priority to European Patent Application No. 21218209.1 filed on Dec. 29, 2021, the disclosure of which is incorporated herein by reference in its entirety.

TECHNICAL FIELD

The present invention relates to storage-stable, radically polymerizable, self-adhesive composites with improved transparency, which are particularly suitable as dental materials, e. g. as dental cements, filling composites or veneering materials, and for the manufacture of inlays, onlays, or crowns.

BACKGROUND

Composites are mainly used in the dental field for the fabrication of direct and indirect fillings, i. e. as direct and indirect filling composites, and as cements. The polymerizable organic matrix of the composites usually consists of a mixture of monomers, initiator components and stabilizers. Mixtures of dimethacrylates are usually used as monomers, which may also contain monofunctional and functionalized monomers. Commonly used dimethacrylates are 2,2-bis[4-(2-hydroxy-3-methacryloyloxy-propyl)phenyl]propane (bis-GMA), 1,6-bis[2-methacryloyloxyethoxycarbonylamino]-2,2,4-trimethylhexane (UDMA), which have high viscosity and give polymers with good mechanical properties and low polymerization shrinkage. Triethylene glycol dimethacrylate (TEGDMA), 1,10-decanediol dimethacrylate ($D_3MA$) or bis(3-methacryloyloxymethyl)tricyclo-[$5.2.1.0^{2,6}$]decane (DCP) are mainly used as reactive diluents. Monofunctional methacrylates, such as p-cumylphenoxyethylene glycol methacrylate (CMP-1E), are also suitable for reducing viscosity and cause a reduction in network density and increased double-bond conversion.

To produce self-adhesive composites, strongly acidic adhesive monomers are used, such as 10-methacryloyloxydecyl dihydrogen phosphate (MDP), which etches the tooth structure and causes adhesion to enamel/dentin by ionic relationship. Adhesive monomers impart self-adhesive properties to composites and thus enable the composites to be used without pretreatment of the tooth structure with an enamel/dentin adhesive, which makes their use particularly attractive.

In addition to the organic matrix, composites contain one or more fillers, which are usually surface-modified with a polymerizable coupling agent, such as 3-methacryloyloxypropyltrimethoxysilane. Fillers improve the mechanical properties (strength, modulus of elasticity, abrasion resistance) and the processing properties (paste consistency, sculptability) of the materials and impart radiopacity.

It is problematic that acidic adhesive monomers often interact adversely with fillers. For example, the acidic adhesion monomers are bound to the surface of the fillers by the formation of insoluble salts, or they form poorly soluble salts during storage with ions released from the fillers. This leads to a significant reduction of the adhesion monomer concentration in the resin matrix, which is associated with a reduction or even a loss of the adhesion properties. Composites with acidic adhesive monomers therefore have only limited storage stability.

Methacrylate-based dental materials are cured by radical polymerization, using radical photoinitiators, thermal initiators, or redox initiator systems, depending on the field of application. Dual-curing systems contain a combination of photoinitiators and redox initiators.

Composite cements usually contain redox systems because they ensure sufficient curing even when light curing is not possible due to insufficient transmittance. Redox initiator systems based on a mixture of dibenzoyl peroxide (DBPO) with tertiary aromatic amines, such as N,N-diethanol-p-toluidine (DEPT), N,N-dimethyl-sym.-xylidine (DMSX) or N,N-diethyl-3,5-di-tert.-butylaniline (DABA), are usually used. Since radical formation in DBPO/amine-based redox initiator systems is greatly impaired by strong acids and thus also by strongly acidic adhesive monomers, redox initiator systems containing cumene hydroperoxide in combination with thioureas, such as acetylthiourea, are preferred.

In order to ensure sufficient storage stability of the redox initiators, redox initiator system-based materials are usually used as so-called 2-component (2C) systems, whereby the oxidizing agent (peroxide or hydroperoxide) and the reducing agent (amines, sulfinic acids, barbiturates, thioureas etc.) are incorporated into separate components. These are mixed together just before use. For mixing, double-push syringes are preferably used, which have separate cylindrical chambers to hold the components. The components are pushed out of the chambers simultaneously by two interconnected pistons and mixed together in a nozzle. To obtain mixtures that are as homogeneous as possible, it is advantageous to mix the components together in approximately equal volume proportions.

Conventional luting cements, such as ZnO eugenol cements, zinc phosphate cements, glass ionomer cements (GIC), and resin modified glass ionomer cements (RMGI), are not suitable for use with double-push syringes because they contain a powder component, which makes mixing of the components considerably more difficult. In addition, glass ionomer cements have only low transparency and relatively poor mechanical properties.

DE 100 21 605 A1 discloses dental filling materials based on epoxy resins containing an ammonium salt, for example ammonium sulfate or ammonium hydrogen sulfate, in combination with a basic calcium salt. Preferred calcium salts are calcium oxide and calcium hydroxide. Upon contact with moisture, the ammonium salt forms ammonia by reacting with the basic calcium salt, which causes the epoxy resin to harden. Gypsum is also formed, which is said to improve the marginal seal of dental and root fillings by expanding during crystallization.

SUMMARY

It is an object of the invention to provide storage-stable, self-adhesive dental composites with good transparency and good mechanical properties, which can be mixed and applied well as 2-component systems using double-push syringes and which are particularly suitable as dental luting cements.

This object is achieved by filler-containing, radically polymerizable compositions comprising at least one acidic, radically polymerizable monomer, at least one fluoroaluminosilicate glass filler and/or radiopaque glass filler and at least one sulfate and/or phosphate which is water-soluble at 20° C. Surprisingly, water-soluble sulfates or phosphates were found to provide a significant increase in the storage stability of compositions containing acidic monomers in combination with at least one fluoroaluminosilicate glass filler and/or radiopaque glass filler.

BRIEF DESCRIPTION OF THE DRAWINGS

Further details, advantages and features will be apparent from the following description of several exemplary embodiments of the invention with reference to the drawing, in which:

FIG. 1 shows a decrease in the concentration of the acidic monomer MDP as a function of storage time in composite pastes with (--▲--; --♦--) and without (-■) ammonium sulfate.

DETAILED DESCRIPTION

According to the invention, preferred sulfates are inorganic salts of sulfuric acid and preferred phosphates are inorganic salts of orthophosphoric acid ($H_3PO_4$). Water-soluble sulfates or phosphates are preferably sulfates or phosphates with a water solubility of at least 100 g/l, preferably of 110 to 1,000 g/l and particularly preferably of 150 to 800 g/l. Preferred water-soluble sulfates are potassium sulfate ($K_2SO_4$; water solubility 111 g/l), sodium sulfate ($Na_2SO_4$; water solubility 170 g/l) and particularly preferably ammonium sulfate ($(NH_4)_2SO_4$; water solubility 754 g/l). Preferred water-soluble phosphates are potassium phosphate ($K_3PO_4$; water solubility 508 g/l), sodium phosphate ($Na_3PO_4$; water solubility 285 g/l) and especially preferably ammonium phosphate ($(NH_4)_3PO_4$; water solubility 580 g/l). All solubility data refer to solubility in water at 20° C.

The one or more water-soluble sulfates and/or water-soluble phosphates are preferably added in a total amount of at least 0.3 wt. % and, in particular, at least 0.4 wt. %. According to the invention, compositions are preferred which contain up to 0.3 to 9.0 wt. %, more preferably 0.4 to 6.0 wt. %, and most preferably from 0.7 to 4.0 wt. % of at least one water-soluble sulfate and/or phosphate. Unless otherwise stated, all percentages herein are based on the total mass of the composition. The sulfates or phosphates may be present in dissolved or preferably in solid form. According to the invention, sulfates are preferred.

The compositions according to the invention contain at least one radically polymerizable monomer, preferably one or more mono- and/or polyfunctional monomers. Polyfunctional monomers are understood to be compounds with two or more, preferably 2 to 4, and particularly preferably 2 radically polymerizable groups. Accordingly, monofunctional monomers have only one radically polymerizable group. Polyfunctional monomers have crosslinking properties and are therefore also referred to as crosslinking monomers. Preferred radically polymerizable groups are (meth) acrylate, (meth)acrylamide, and vinyl groups.

According to the invention, a distinction is made between monomers containing acid groups and monomers which do not contain acid groups. The compositions according to the invention contain at least one monomer without acid groups and at least one monomer and/or oligomer with acid groups. According to the invention, compositions are preferred which contain monomers with and monomers without acid groups in a weight ratio of from 1:5 to 1:36, particularly preferably from 1:6 to 1:25, and most preferably from 1:7 to 1:20.

Monomers without an Acid Group

Preferred are compositions comprising at least one (meth) acrylate, more preferably at least one monofunctional or polyfunctional methacrylate, most preferably at least one monofunctional or difunctional methacrylate or a mixture thereof.

Preferred monofunctional (meth)acrylates are benzyl, tetrahydrofurfuryl or isobornyl (meth)acrylate, p-cumylphenoxyethylene glycol methacrylate (CMP-1E) and 2-([1,1'-biphenyl]-2-oxy)ethyl methacrylate (MA-836), tricyclodecane methyl (meth)acrylate, and 2-(2-biphenyloxy)ethyl (meth)acrylate. CMP-1E and MA-836 are particularly preferred.

According to one embodiment, the compositions according to the invention preferably comprise at least one functionalized monofunctional (meth)acrylate. Functionalized monomers are understood to be those monomers which, in addition to at least one radically polymerizable group, carry at least one functional group, preferably a hydroxyl group. Preferred functionalized mono(meth)acrylates are 2-hydroxyethyl- and hydroxyethylpropyl(methacrylate) as well as 2-acetoxyethyl methacrylate. Hydroxyethyl methacrylate is particularly preferred. The monomers containing an acid group that are mentioned below are not functionalized monomers within the meaning of the invention.

Preferred di- and polyfunctional (meth)acrylates are bisphenol-A-dimethacrylate, bis-GMA (an addition product of methacrylic acid and bisphenol-A-diglycidyl ether), ethoxy- or propoxylated bisphenol-A-dimethacrylates, e. g. the bisphenol A dimethacrylate SR-348c (Sartomer) with 3 ethoxy groups or 2,2-bis[4-(2-methacryloyloxypropoxy)phenyl] propane, urethanes of 2-(hydroxymethyl)acrylic acid and diisocyanates, such as 2,2,4-trimethylhexamethylene diisocyanate or isophorone diisocyanate, UDMA (an addition product of 2-hydroxyethyl methacrylate and 2,2,4-trimethylhexamethylene-1,6-diisocyanate), tetramethylxylylene diurethane ethylene glycol di(meth)acrylate or tetramethylxylylene diurethane-2-methylethylene glycol di(meth)acrylate (V380), di-, tri- or tetraethylene glycol dimethacrylate, trimethylolpropane trimethacrylate, pentaerythritol tetramethacrylate as well as glycerol di- and trimethacrylate, 1,4-butanediol dimethacrylate, 1,10-decanediol dimethacrylate ($D_3MA$), bis(methacryloyloxymethyl)tricyclo-[5.2.1.$0^{2,6}$]decane (DCP), polyethylene glycol or polypropylene glycol dimethacrylates, such as polyethylene glycol 200-dimethacrylate or polyethylene glycol 400-dimethacrylate (PEG-200- or PEG-400-DMA) or 1,12-dodecanediol dimethacrylate. Bis-GMA, UDMA, V-380, triethylene glycol dimethacrylate (TEGDMA) and PEG-400-DMA (NK ester 9G) are particularly preferred.

The monomer tetramethylxylylene diurethane ethylene glycol di(meth)acrylate or tetramethylxylylene diurethane 2-methylethylene glycol diurethane di(meth)acrylate (V380) has the following formula:

V380

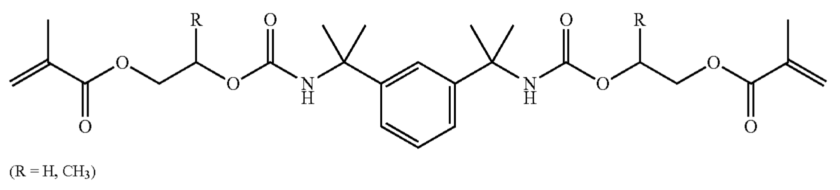

($R = H, CH_3$)

In the formula shown, the radicals R are each independently H or $CH_3$, and the radicals may have the same meaning or different meanings. Preferably, a mixture is used which contains molecules in which both radicals are H, molecules in which both radicals are $CH_3$, and molecules in which one radical is H and the other radical is $CH_3$, the ratio of H to $CH_3$ preferably being 7:3. Such a mixture is obtainable, for example, by reacting 1,3-bis(1-isocyanato-1-methylethyl)benzene with 2-hydroxypropyl methacrylate and 2-hydroxyethyl methacrylate.

Other preferred difunctional monomers are radically polymerizable pyrrolidones, such as 1,6-bis(3-vinyl-2-pyrrolidonyl)hexane, or commercially available bisacrylamides such as methylene or ethylene bisacrylamide, as well as bis(meth)acrylamides, such as N,N'-diethyl-1,3-bis(acrylamido)propane, 1,3-bis(methacrylamido)propane, 1,4-bis(acrylamido)butane or 1,4-bis(acryloyl)piperazine, which can be synthesized by reaction from the corresponding diamines with (meth)acrylic acid chloride. N,N'-diethyl-1,3-bis(acrylamido)propane (V-392) is particularly preferred. These monomers are characterized by high hydrolytic stability.

Monomers and Oligomers with Acid Groups

The compositions according to the invention contain at least one acidic radically polymerizable monomer. Acidic radically polymerizable monomers are monomers which, in addition to at least one radically polymerizable group, contain at least one acid group, preferably a phosphoric ester, phosphonic acid or carboxy group, particularly preferably at least one phosphoric ester group. Acidic monomers are also referred to herein as adhesion components or adhesion monomers. Preferred are adhesion monomers which contain at least one (meth)acrylate and, in particular, methacrylate group as a -radically polymerizable group.

Preferred monomers containing at least one acid group are phosphoric ester and phosphonic acid monomers. Particularly preferred are 2-methacryloyloxyethylphenyl hydrogen phosphate, 10-methacryloyloxydecyl dihydrogen phosphate (MDP), glycerol dimethacrylate dihydrogen phosphate or dipentaerythritol pentamethacryloyloxy phosphate, 4-Vinylbenzylphosphonic acid, 2-[4-(dihydroxyphosphoryl)-2-oxa-butyl]-acrylic acid or hydrolysis-stable esters, such as 2-[4-(dihydroxyphosphoryl)-2-oxa-butyl]-acrylic acid 2,4,6-trimethylphenyl ester. MDP, 2-methacryloyloxyethylphenyl hydrogen phosphate and glycerol dimethacrylate dihydrogen phosphate are particularly preferred.

Other preferred monomers containing an acid group are polymerizable monomers that contain at least one COOH group. Particularly preferred are 4-(meth)acryloyloxyethyltrimellitic anhydride, 10-methacryloyloxydecylmalonic acid, N-(2-hydroxy-3-methacryloyloxypropyl)-N-phenylglycine and 4-vinylbenzoic acid.

According to a further preferred embodiment, the compositions according to the invention additionally contain at least one acidic, radically polymerizable oligomer. Oligomers are understood to be polymers with a degree of polymerization $P_n$ of 2 to 100 ($P_n=M_n/M_u$; $M_n$: number-average polymer molar mass, $M_u$: molar mass of the monomer unit). Acidic radically polymerizable oligomers have at least one acid group, preferably a carboxyl group, and at least one radically polymerizable group, preferably a (meth)acrylate group and in particular a methacrylate group.

Oligomers containing acid groups preferred according to the invention are oligomeric carboxylic acids, such as polyacrylic acid, preferably with a number average molecular weight $M_n$ of less than 7,200 g/mol, preferably less than 7,000 g/mol and particularly preferably less than 6,800 g/mol, where $M_n$ is preferably in a range from 800 to 7,200 g/mol, more preferably from 500 to 7,000 g/mol, and more particularly preferably from 500 to 6,800 g/mol. Oligomeric carboxylic acids containing (meth)acrylate groups are particularly preferred. These can be obtained, for example, by reacting oligomeric polyacrylic acid with glycidyl methacrylate or 2-isocyanatoethyl methacrylate.

Unless otherwise stated, the molar mass of oligomers and polymers herein is the number-average molar mass, the absolute values of which can be determined by the known methods of freezing point depression (cryoscopy), boiling point elevation (ebullioscopy) or through the depression of the vapor pressure (vapor pressure osmometry). Preferably, the number average molecular weight of oligomers and polymers is determined by gel permeation chromatography (GPC). This is a relative method in which molecules are separated on the basis of their size, more precisely on the basis of their hydrodynamic volume. The absolute molar mass is determined by calibration with known standards.

The compositions according to the invention also preferably contain water. It has been found that a water content of 1 to 7 wt. %, particularly preferably 1 to 5 wt. %, in each case based on the total mass of the composition, brings about an improvement in the bonding effect to dentin and enamel.

The compositions according to the invention further comprise at least one initiator for initiating the radical polymerization, preferably a photoinitiator. Preferred photoinitiators are benzophenone, benzoin and derivatives thereof, α-diketones or derivatives thereof, such as 9,10-phenanthrenequinone, 1-phenyl-propane-1,2-dione, diacetyl and 4,4'-dichlorobenzil. Particularly preferably, camphorquinone (CQ) and 2,2-dimethoxy-2-phenyl-acetophenone are used, and most preferably α-diketones are used in combination with amines as reducing agents, such as ethyl 4-(dimethylamino)benzoate (EDMAB), N,N-dimethylaminoethyl methacrylate, N,N-dimethyl-sym.-xylidine or triethanolamine. Further preferred are Norrish type I photoinitiators, especially acyl or bisacyl phosphine oxides and most preferably monoacyltrialkyl, diacyldialkylgermanium and tetraacylgermanium compounds, such as benzoyltrimethylgerman, dibenzoyldiethylgerman, bis(4-methoxybenzoyl)diethylgerman (Ivocerin®), tetrabenzoylgerman or tetrakis(o-methylbenzoyl)german. Mixtures of the various photoinitiators can also be used, such as bis(4-methoxybenzoyl)diethylgerman or tetrakis(o-methylbenzoyl)german in combination with camphorquinone and 4-dimethylaminobenzoic acid ethyl ester.

Further preferred are compositions containing a redox initiator for initiating radical polymerization, preferably a redox initiator based on an oxidizing agent and a reducing agent. Preferred oxidizing agents are peroxides and, in particular, hydroperoxides. A particularly preferred peroxide is benzoyl peroxide. Preferred hydroperoxides are the low-odor cumene hydroperoxide derivatives disclosed in EP 3 692 976 A1 and corresponding U.S. Pat. No. 11,357,709 B2, which US patent is hereby incorporated by reference in its entirety, the oligomeric CHP derivatives disclosed in EP 21315089.9, and in particular 4-(2-hydroperoxypropan-2-yl)phenylpropionate and cumene hydroperoxide (CHP).

Preferred reducing agents for combination with peroxides are tertiary amines, such as N,N-dimethyl-p-toluidine, N,N-dihydroxyethyl-p-toluidine, p-dimethylaminobenzoic acid ethyl ester or other aromatic dialkylamines, ascorbic acid, sulfinic acids, thiols, and/or hydrogen silanes.

Preferred reducing agents for combination with hydroperoxides are thiourea derivatives, in particular the compounds listed in paragraph [0009] of EP 1 754 465 A1 and corresponding US 2007040151 A1, which US published application is hereby incorporated by reference in its entirety. Particularly preferred are methyl-, ethyl-, allyl-, butyl-, hexyl-, octyl-, benzyl-, 1,1,3-trimethyl-, 1,1-diallyl-, 1,3-diallyl-, 1-(2-pyridyl)-2-thiourea, acetyl-, propanoyl-, butanoyl-, pentanoyl-, hexanoyl-, heptanoyl-, octanoyl-, nonanoyl-, decanoyl-, benzoylthiourea, and mixtures thereof. Quite particularly preferred are acetyl-, allyl-, pyridyl- and phenylthiourea as well as hexanoylthiourea and mixtures thereof as well as polymerizable thiourea derivatives, such as N-(2-methacryloyloxyethoxysuccinoyl)-thiourea and N-(4-vinylbenzoyl)-thiourea). In addition, a combination of one or more of said thiourea derivatives with one or more imidazoles may advantageously be used. Preferred imidazoles are 2-mercapto-1-methylimidazole or 2-mercaptobenzimidazole.

According to a preferred embodiment, the compositions according to the invention may further comprise, in addition to at least one hydroperoxide and at least one thiourea derivative, at least one transition metal compound for accelerating curing. Transition metal compounds preferred according to the invention are compounds derived from transition metals having at least two stable oxidation states. Particularly preferred are compounds of the elements copper, iron, cobalt, nickel, and manganese. These metals have the following stable oxidation states: Cu(I)/Cu(II), Fe(II)/Fe(III), Co(II)/Co(III), Ni(II)/Ni(III), Mn(II)/Mn(III). Compositions containing at least one copper compound are particularly preferred. The transition metal compounds are preferably used in catalytic amounts, particularly preferably in an amount of 10 to 200 ppm. These amounts do not lead to discoloration of the dental materials. Because of their good monomer solubility, the transition metals are preferably used in the form of their acetylacetonates, 2-ethylhexanoates or THF adducts. Further preferred are their complexes with polydentate ligands such as 2-(2-aminoethylamino)ethanol, triethylenetetramine, dimethylglyoxime, 8-hydroxyquinoline, 2,2'-bipyridine or 1,10-phenanthroline. A particularly preferred initiator according to the invention is a mixture of cumene hydroperoxide (CHP) with at least one of the above-mentioned thiourea derivatives and copper (II) acetylacetonate.

The compositions according to the invention preferably do not contain barbituric acid or barbituric acid derivatives such as 1,3,5-trimethylbarbituric acid, 1-benzyl-5-phenylbarbituric acid, 5-butylbarbituric acid or 1-cyclohexyl-5-ethylbarbituric acid. Compositions containing barbiturates have unsatisfactory storage stability because barbiturates form polymerization-initiating radicals by oxidation with atmospheric oxygen.

In addition, barbiturates have adverse physiological effects such as bradycardia, hypotension, or blood disorders.

The compositions according to the invention contain at least one inorganic filler. Compositions containing fillers are referred to as composites. Preferred are compositions containing at least one fluoroaluminosilicate glass filler (FAS filler) and/or a radiopaque glass filler.

Preferred radiopaque glass fillers have the following composition (wt. %): $SiO_2$: 20-80; $B_2O_3$: 2-15, BaO or SrO: 0-40; $Al_2O_3$: 2-20; CaO and/or MgO: 0-20; $Na_2O$, $K_2O$, $Cs_2O$: 0-10 each; $WO_3$: 0-20; ZnO: 0-20; $La_2O_3$: 0-10; $ZrO_2$: 0-15; $P_2O_5$: 0-30; $Ta_2O_5$, $Nb_2O_5$ or $Yb_2O_3$: 0-5; and $CaF_2$ and/or $SrF_2$ 0-10. Particularly preferred are radiopaque glass fillers having the composition (wt. %): $SiO_2$: 50-75; $B_2O_3$: 2-15; BaO or SrO: 2-35; $Al_2O_3$: 2-15; CaO and/or MgO: 0-10; and $Na_2O$: 0-10.

Particularly preferred FAS fillers have the following composition (wt. %): $SiO_2$: 20-35; $Al_2O_3$: 15-35; BaO or SrO: 10-25; CaO: 0-20; ZnO: 0-15; $P_2O_5$: 5-20; $Na_2O$, $K_2O$, $Cs_2O$: 0-10 each; and $CaF_2$: 0.5-20. Particularly preferred are FAS fillers with the composition (wt. %): $SiO_2$: 20-30; $Al_2O_3$: 20-30; BaO or SrO: 10-25; CaO: 5-20; $P_2O_5$: 5-20; $Na_2O$: 0-10; and $CaF_2$: 5-20.

All data refer to the total mass of the glass, with all components except fluorine being calculated as oxides, as is usual for glasses and glass ceramics.

The FAS fillers and radiopaque glass fillers preferably have an average particle size of 0.2 to 20 μm and particularly preferably of 0.4 to 5 μm.

The compositions according to the invention preferably contain from 25 to 80 wt. %, more preferably from 30 to 75 wt. %, and most preferably from 40 to 70 wt. % of FAS filler and/or radiopaque glass filler, in each case based on the total mass of the composition.

In addition to the aforementioned FAS and radiopaque glass fillers, the compositions according to the invention may contain further fillers.

Preferred further fillers are metal oxides, particularly preferably mixed oxides, containing 60 to 80 wt. % $SiO_2$ and at least one of the metal oxides $ZrO_2$, $Yb_2O_3$, ZnO, $Ta_2O_5$, $Nb_2O_5$ and/or $La_2O_3$, so that the total amount adds up to 100%. Mixed oxides such as $SiO_2$—$ZrO_2$ are accessible, for example, by hydrolytic co-condensation of metal alkoxides. The metal oxides preferably have an average particle size of 0.05 to 10 μm, particularly preferably of 0.1 to 5 μm.

Other preferred additional fillers are fumed silica or precipitated silica with a primary particle size of 0.01-0.15 μm, as well as quartz or glass ceramic powder with a particle size of 0.1 to 15 μm, preferably from 0.2 to 5 μm, and ytterbium trifluoride. The ytterbium trifluoride preferably has a particle size of 80 to 900 nm and particularly preferably of 100 to 300 nm. These fillers are preferably used in an amount of 0.1 to 40 wt. %, more preferably 0.2 to 35 wt. % and very particularly preferably in an amount of 0.3 to 25 wt. %, in each case based on the total mass of the composition.

In addition, so-called composite fillers are preferred as further fillers. These are also referred to as isofillers. These are splinter-like polymers which in turn contain a filler, preferably pyrogenic $SiO_2$ and/or ytterbium trifluoride. Preferred are polymers based on dimethacrylates. For the production of isofillers, the one or more fillers are incorporated, for example, into a dimethacrylate resin matrix, and the resulting composite paste is subsequently thermally polymerized and then ground.

A composite filler preferred according to the invention can be prepared, for example, by thermally curing a mixture of bis-GMA (8.80 wt. %), UDMA (6.60 wt. %), 1,10-decanediol dimethacrylate (5.93 wt. %), dibenzoyl peroxide+2,6-di-tert.-butyl-4-methylphenol (0.67 wt. % combined), glass filler (average grain size 0.4 μm; 53.0 wt. %) and $YbF_3$ (25.0 wt. %) and then grinding the cured material to the desired grain size. All percentages refer to the total mass of the composite filler.

So-called inertized fillers can also be used as further fillers. These are glass fillers whose surface is coated with a diffusion barrier layer, e. g. on a sol-gel basis, or with a polymer layer, e. g. PVC. Preferred fillers are those described in EP 2 103 296 A1.

To improve the bond between filler and matrix, the fillers are preferably surface-modified with methacrylate functionalized silanes, such as 3-methacryloyloxypropyltrimethoxysilane.

The compositions according to the invention preferably contain 1 to 50 wt. %, more preferably 1.5 to 40 wt. %, and most preferably 2 to 30 wt. % of one or more further fillers, preferably one or more metal oxides, pyrogenic silica and/or precipitated silica, in each case based on the total mass of the composition.

Unless otherwise stated, all particle sizes herein are volume-averaged particle sizes (D50 values), i. e. 50% of the total volume common to all particles is contained in particles having a diameter smaller than the stated value. The D10 value is accordingly the volumetric diameter at which 10% of the total filler volume is smaller than the specified value.

Particle size determination in the range from 0.1 μm to 1000 μm is preferably carried out by means of static light scattering (SLS), for example with an LA-960 static laser scattering particle size analyzer (Horiba, Japan) or with a Microtrac S100 particle size analyzer (Microtrac, USA). Here, a laser diode with a wavelength of 655 nm and an LED with a wavelength of 405 nm are used as light sources. The use of two light sources with different wavelengths enables the measurement of the entire particle size distribution of a sample in only one measurement run, whereby the measurement is carried out as a wet measurement. For this purpose, an aqueous dispersion of the filler is prepared and its scattered light is measured in a flow cell. The scattered light analysis for calculating particle size and particle size distribution is carried out according to the Mie theory according to DIN/ISO 13320. The measurement of the particle size in a range from 1 nm to 0.1 μm is preferably carried out by dynamic light scattering (DLS) of aqueous particle dispersions, preferably with a He—Ne laser with a wavelength of 633 nm, at a scattering angle of 90° and at 25° C., e. g. with a Malvern Zetasizer Nano ZS (Malvern Instruments, Malvern UK).

In the case of aggregated and agglomerated particles, the primary particle size can be determined from TEM images. Transmission electron microscopy (TEM) is preferably performed using a Philips CM30 TEM at an accelerating voltage of 300 kV. For sample preparation, drops of particle dispersion are deposited on a 50 Å thick copper grid (mesh size 300 mesh) coated with carbon, followed by evaporation of the solvent. The particles are counted and the arithmetic mean is calculated.

The compositions according to the invention may also contain additional additives, in particular stabilizers, colorants, phase transfer catalysts, microbicidal agents, fluoride ion-donating additives, such as fluoride salts, in particular NaF or ammonium fluoride, or fluorosilanes, optical brighteners, plasticizers, and/or UV absorbers.

Preferably, the compositions according to the invention comprise:

5 to 60 wt. %, preferably 8 to 45 wt. %, and particularly preferably 10 to 35 wt. % of at least one radically polymerizable monomer without acid groups, 1 to 15 wt. %, preferably 2 to 12 wt. %, and particularly preferably 3 to 10 wt. % of at least one radically polymerizable monomer with an acid group, 25 to 80 wt. %, preferably 30 to 75 wt. %, and particularly preferably 40 to 70 wt. % of at least one FAS filler and/or radiopaque glass filler, 0.1 to 8 wt. %, preferably 0.5 to 6 wt. %, and particularly preferably 1 to 5 wt. % by weight of at least one initiator for the radical polymerization, and 0.3 to 9 wt. %, preferably 0.4 to 6 wt. % and particularly preferably 0.7 to 4.0 wt. % of at least one water-soluble sulfate and/or phosphate.

Unless otherwise stated, all percentages herein refer to the total mass of the composition. All amounts for radically polymerizable monomers (poly- and monofunctional) refer only to monomers without an acid group and do not include monomers containing an acid group.

The initiator can be a redox initiator, a photoinitiator, or an initiator for dual curing. The amounts mentioned include all initiator components, i. e. the initiators themselves and, if necessary, reducing agents, transition metal compound, etc. According to the invention, compositions containing at least one redox initiator or at least one redox initiator and at least one photoinitiator are preferred.

According to the invention, those compositions are particularly preferred which comprise the following ingredients:

a) 0.3 to 9 wt. %, preferably 0.4 to 6 wt. %, and particularly preferably 0.7 to 4.0 wt. % of at least one water-soluble sulfate and/or phosphate, b) 5 to 40 wt. %, preferably from 8 to 35 wt. %, and particularly preferably from 10 to 30 wt. % of at least one polyfunctional monomer without acid groups, c) 1 to 15 wt. %, preferably 2 to 12 wt. %, and particularly preferably 3 to 10 wt. % of at least one radically polymerizable monomer with an acid group, d) 0 to 10 wt. %, preferably 0 to 8 wt. %, and particularly preferably 0 to 5 wt. % of one or more oligomeric carboxylic acids, e) optionally 0.1 to 20 wt. %, preferably from 0.5 to 15 wt. %, and particularly preferably 1 to 10 wt. % of one or more monofunctional monomers without acid groups, f) 25 to 80 wt. %, preferably 30 to 75 wt. %, and particularly preferably 40 to 70 wt. % of at least one FAS filler and/or radiopaque glass filler, g) optionally 1 to 50 wt. %, preferably 1.5 to 40 wt. % and particularly preferably 2 to 30 wt. % of one or more additional fillers, (h) 0.1 to 8 wt. %, preferably 0.5 to 6 wt. %, and particularly preferably 1 to 5 wt. % of at least one initiator for the radical polymerization, i) 0 to 20 wt. %, preferably 0.2 to 10 wt. %, and particularly preferably 1 to 7 wt. % of water, and j) 0.01 to 5 wt. %, preferably 0.1 to 3 wt. %, and particularly preferably 0.1 to 2 wt. % of one or more additives, in each case based on the total mass of the composition.

Compositions containing a redox initiator are also referred to as self-curing. They are preferably used in the form of two spatially separated components, i. e. as a 2-component system (2C system). Oxidizing and reducing agents are incorporated into separate components of the composition. One component, the so-called catalyst paste, contains the oxidizing agent, preferably a peroxide or hydroperoxide, and the second component, the so-called base paste, contains the corresponding reducing agent and optionally a photoinitiator and optionally catalytic amounts of a transition metal compound. Polymerization is initiated by mixing the components. Compositions containing both a redox initiator and a photoinitiator are referred to as dual-curing.

In two-component compositions, the water-soluble sulfate and/or phosphate is preferably added to the component containing the strongly acidic adhesive monomer, the FAS filler, and/or the radiopaque glass filler.

According to the invention, 2-component systems are preferred. They are preferably self-curing or dual-curing. The pastes are mixed together shortly before use, preferably with a double-push syringe.

The catalyst paste preferably has the following composition:

a) 0.3 to 9 wt. %, preferably 0.4 to 6 wt. %, and particularly preferably 0.7 to 4.0 wt. % of at least one water-soluble sulfate and/or phosphate,
b) 5 to 40 wt. %, preferably from 8 to 35 wt. %, particularly preferably from 10 to 30 wt. % of at least one polyfunctional monomer,
c) 2 to 30 wt. %, preferably 4 to 24 wt. %, and particularly preferably 6 to 20 wt. % of at least one monomer containing acid groups,
d) 0 to 20 wt. %, preferably 0 to 16 wt. %, and particularly preferably 0 to 10 wt. % of one or more oligomeric carboxylic acids,
e) optionally 0.1 to 20 wt. %, preferably 0.5 to 15 wt. %, and particularly preferably 1 to 10 wt. % of one or more monofunctional monomers,
f) 25 to 80 wt. %, preferably 30 to 75 wt. %, and particularly preferably 40 to 70 wt. % of at least one FAS and/or glass filler,
g) optionally 1 to 50 wt. %, preferably 1.5 to 40 wt. %, and particularly preferably 2 to 30 wt. % of one or more additional fillers,
h) 0.01 to 16 wt. %, preferably 0.02 to 12 wt. %, and particularly preferably 0.03 to 10 wt. % of at least one peroxide and/or hydroperoxide and optionally at least one photoinitiator,
i) 0 to 20 wt. %, preferably 0.2 to 10 wt. %, and particularly preferably 1 to 7 wt. % of water, and
j) 0.001 to 5 wt. % by weight, preferably 0.03 to 3 wt. %, and particularly preferably 0.05 to 2 wt. % of one or more additives, in each case based on the total mass of the catalyst paste.

The base paste preferably has the following composition:

a) not applicable,
b) from 5 to 40 wt. %, preferably from 8 to 35 wt. %, and particularly preferably from 10 to 30 wt. % of at least one polyfunctional monomer,
c) not applicable,
d) not applicable,
e) optionally 0.1 to 20 wt. %, preferably 0.5 to 15 wt. %, and particularly preferably 1 to 10 wt. % of one or more monofunctional monomers,
f) 25 to 80 wt. %, preferably 30 to 75 wt. %, and particularly preferably 40 to 70 wt. % of at least one FAS and/or glass filler,
g) optionally 1 to 50 wt. %, preferably 1.5 to 40 wt. %, and particularly preferably 2 to 30 wt. % of one or more additional fillers,
h) 0.01 to 16 wt. %, preferably 0.02 to 12 wt. %, and particularly preferably 0.03 to 10 wt. % of at least one suitable reducing agent and optionally a photoinitiator,
i) 0 to 20 wt. %, preferably 0.2 to 10 wt. %, and particularly preferably 1 to 7 wt. % of water, and
j) 0.001 to 5 wt. % by weight, preferably 0.03 to 3 wt. %, and particularly preferably 0.05 to 2% of one or more additives, in each case based on the total mass of the base paste.

For application, the catalyst and base paste are preferably mixed together in approximately equal proportions. They are therefore particularly suitable for application with a double-push syringe.

Double-push syringes have two separate cylindrical chambers for holding base paste and catalyst paste. The components are pressed out of the chambers simultaneously by two interconnected pistons and are preferably forced through a mixing cannula and mixed together therein. For pressing out the pastes, the syringe can be inserted into a so-called hand dispenser, which improves handling of the syringes.

The compositions according to the invention are characterized by high storage stability and improved transparency, preferably greater than 10%, and good self-adhesion to enamel/dentin. They are particularly suitable as dental materials for intraoral use by the dentist for the restoration of damaged teeth (therapeutic use), especially as dental cements, coating materials or veneering materials, filling composites and particularly as luting cements. The transparency is determined in the manner described in the examples.

For the treatment of damaged teeth, these are preferably prepared in a first step by the dentist. Subsequently, at least one composition according to the invention is applied to or into the prepared tooth. Thereafter, the composition can be cured directly, preferably by irradiation with light of a suitable wavelength, for example when restoring cavities. Alternatively, a dental restoration, for example an inlay, onlay, veneer, crown, bridge, framework, or dental ceramic, is placed in or applied to the prepared tooth. Subsequent curing of the composition is preferably done by light and/or self-curing. The dental restoration is attached to the tooth in this process.

The compositions according to the invention can also be used as extraoral materials (non-therapeutic), for example in the fabrication or repair of dental restorations. They are also suitable as materials for the fabrication and repair of inlays, onlays, crowns, or bridges.

For the production of dental restorations such as inlays, onlays, crowns, or bridges, at least one composition according to the invention is formed into the desired dental restoration in a manner known per se and then cured. The curing can be done by light, through self-curing, or preferably thermally.

In the repair of dental restorations, the compositions according to the invention are placed onto the restoration to be repaired, for example to repair gaps or to bond fragments, and then cured.

The invention is explained in more detail below with reference to figures and examples of embodiments.

FIG. 1 shows the decrease in the concentration of the acidic monomer MDP as a function of storage time in composite pastes with (--▲--; --♦--) and without (--■--) ammonium sulfate.

Example 1

Investigation of the Storage Stability of Self-Adhesive Composites with and without Ammonium Sulfate Composite pastes C-1 to C-3 with the compositions given in Table 1 (all data in wt. %) were prepared from the following components: Glass filler GM 27884, silanized (Schott AG; mean particle size 1 μm; specific surface area (BET DIN ISO 9277) 3.9 $m^2/g$; composition (wt. %): $Al_2O_3$: 10, $B_2O_3$: 10, BaO: 25 and $SiO_2$: 55), pyrogenic silica HDK 2000 (Wacker Chemie AG; BET surface area 120 $m^2/g$), 10-methacryloyloxydecyl dihydrogen phosphate (MDP, Orgentis), triethylene glycol dimethacrylate (TEGDMA), NK ester 9G (polyethylene glyco-400-dimethacrylate, Kowa Europa GmbH), V-392 (N,N'-diethyl-1,3-bis(acrylamido)propane, Ivoclar Vivadent AG), BHT (2,6-di-tert-butyl-p-cresol) and ammonium sulfate $(NH_4)_2SO_4$ (Aldrich).

TABLE 1

| Composition of the composite pastes | | | |
|---|---|---|---|
| | C-1*) (without $(NH_4)_2SO_4$) | C-2 | C-3 |
| TEGDMA | 10.96 | 10.62 | 10.66 |
| NK ester 9G | 2.34 | 2.36 | 2.37 |
| V-392 | 14.39 | 14.55 | 14.60 |
| MDP | 3.29 | 3.44 | 3.34 |
| BHT | 0.05 | 0.03 | 0.034 |
| $(NH_4)_2SO_4$ | 0 | 1.41 | 0.456 |
| HDK 2000 | 4.00 | 4.00 | 4.00 |
| GM 27884 | 65.00 | 63.59 | 64.54 |

*)comparative example

Pastes C-1 (without $(NH_4)_2SO_4$), C-2 (1.41% $(NH_4)_2SO_4$), and C-3 (0.456% $(NH_4)_2SO_4$) were stored at room temperature for a period of 16 weeks and the content of MDP was repeatedly determined by $^{31}$P-NMR spectroscopy. For $^{31}$P-NMR measurement, 1.5 g of each sample to be analyzed was weighed into a centrifuge tube and mixed with 1.5 ml of a solution of 0.1 g triphenylphosphine in 10 ml of deuterated acetone (acetone-$d_6$) as an internal standard. The resulting suspension was shaken using a platform shaker (Vibramax, Heidolph Instruments GmbH & Co. KG, Schwabach, Germany) for at least 5 min and then centrifuged at 3,500 rpm for 15 min. The supernatant was transferred to an NMR sample tube using a disposable pipette. The measurement was performed using an Avance DPX 400 (Bruker Spectrospin) 400 MHz—nuclear magnetic resonance spectrometer. The MDP concentration was calculated from the ratio of the peak areas with respect to the inner standard.

FIG. 1 shows the change over time of the content of MDP in the composite pastes with and without $(NH_4)_2SO_4$.

The results shown in FIG. 1 demonstrate a significantly improved storage stability of the composites C-2 and C-3 with $(NH_4)_2SO_4$. The composite C-1 without $(NH_4)_2SO_4$ shows an almost complete decrease of the available MDP after only 10 weeks, while in the composite pastes C-2 and C-3 with $(NH_4)_2SO_4$ a relevant content of MDP was still detectable after 16 weeks.

The invention claimed is:

1. A radically polymerizable composition comprising at least one acidic radically polymerizable monomer;

at least one fluoroaluminosilicate glass filler and/or radiopaque glass filler; and at least one water-soluble sulfate and/or phosphates wherein the radiopaque glass filler comprises the composition: $SiO_2$: 20-80 wt. %; $B_2O_3$: 2-15 wt. %; BaO or SrO: 0-40 wt. %; $Al_2O_3$: 2-20 wt. %; CaO and/or MgO: 0-20 wt. %; $Na_2O$, $K_2O$, $Cs_2O$: 0-10 wt. % each; $WO_3$: 0-20 wt. %; ZnO: 0-20 wt. %; $La_2O_3$: 0-10 wt. %; $ZrO_2$: 0-15 wt. %; $P_2O_5$: 0-30 wt. %; $Ta_2O_5$, $Nb_2O_5$ or $Yb_2O_3$: 0-5 wt. %; and $CaF_2$ and/or $SrF_2$: 0-10 wt. %; and/or wherein the fluoroaluminosilicate glass filler comprises the composition: $SiO_2$: 20-35 wt. %; $Al_2O_3$: 15-35 wt. %; BaO or SrO: 10-25 wt. %; CaO: 0-20 wt. %; ZnO: 0-15 wt. %; $P_2O_5$: 5-20 wt. %; $Na_2O$, $K_2O$, $Cs_2O$: 0-10 wt. % each; and $CaF_2$: 0.5-20 wt. %;

all figures being based on the total mass of the glass, and all components except fluorine being calculated as oxides.

2. The composition according to claim 1, wherein the at least one water-soluble sulfate comprises at least one inorganic salt of sulfuric acid having a water solubility of at least 100 g/l at 20° C. and/or wherein the at least one water-soluble phosphate comprises at least one inorganic salt of orthophosphoric acid with a water solubility of at least 100 g/l at 20° C.

3. The composition according to claim 1, wherein the at least one water-soluble sulfate comprises sulfate potassium sulfate, sodium sulfate, ammonium sulfate or a mixture thereof, and/or wherein the at least one water-soluble phosphate comprises potassium phosphate, sodium phosphate, ammonium phosphate or a mixture thereof.

4. The composition according to claim 1 comprising 0.3 to 9.0 wt. % of the at least one water-soluble sulfate and/or phosphate, based on total mass of the composition.

5. The composition according to claim 4, which comprises 5 to 60 wt. % of at least one radically polymerizable monomer without acid groups, 1 to 15 wt. % of at least one radically polymerizable monomer with an acid group, 25 to 80 wt. % of at least one fluoroaluminosilicate glass filler and/or radiopaque glass filler, 0.1 to 8 wt. % of at least one initiator for the radical polymerization, and 0.3 to 9 wt. % of at least one water-soluble sulfate and/or phosphate, in each case based on the total mass of the composition.

6. The composition according to claim 5, which comprises a) 0.3 to 9 wt. % of at least one water-soluble sulfate and/or phosphate, b) 5 to 40 wt. % of at least one polyfunctional monomer without acid groups, c) 1 to 15 wt. % by weight of at least one radically polymerizable monomer containing an acid group, d) 0 to 10 wt. % of one or more oligomeric carboxylic acids, e) optionally 0.1 to 20 wt. % of one or more monofunctional monomers without acid groups, f) 25 to 80 wt. % of at least one fluoroaluminosilicate glass filler and/or radiopaque glass filler, g) optionally 1 to 50 wt. % of one or more additional fillers, h) 0.1 to 8 wt. % of an initiator for the radical polymerization, i) 0 to 20 wt. % of water, and j) 0.01 to 5 wt. % of one or more additives, in each case based on the total mass of the composition.

7. The composition according to claim 6, wherein the at least one polyfunctional monomer without acid groups (b) comprises at least one monomer selected from bisphenol A dimethacrylate, bis-GMA (an addition product of methacrylic acid and bisphenol A diglycidyl ether), ethoxy- or propoxylated bisphenol A dimethacrylates, such as bisphenol A dimethacrylate with 3 ethoxy groups or 2,2-bis[4-(2-methacryloyloxypropoxy)-phenyl]propane, urethanes of 2-(hydroxymethyl)acrylic acid and diisocyanates, such as 2,2,4-trimethylhexamethylene diisocyanate or isophorone diisocyanate, UDMA (an addition product of 2-hydroxyethyl methacrylate and 2,2,4-trimethylhexamethylene-1,6-diisocyanate), tetramethylxylylene diurethane ethylene glycol di(meth)acrylate or tetramethylxylylene diurethane-2-methylethylene glycol diurethane di(meth)acrylate (V380), di-, tri- or tetraethylene glycol dimethacrylate, trimethylolpropane trimethacrylate, pentaerythritol tetramethacrylate, and glycerol di- and trimethacrylate, 1,4-butanediol dimethacrylate, 1,10-decanediol dimethacrylate (D3MA), bis(methacryloyloxymethyl)tricyclo-[5.2.1.0$^{2,6}$]decane (DCP), polyethylene glycol or polypropylene glycol dimethacrylates, such as polyethylene glycol 200-dimethacrylate (PEG-200-DMA) or polyethylene glycol 400-dimethacrylate (PEG-400-DMA), 1,12-dodecanediol dimethacrylate, radically polymerizable pyrrolidones, such as, 1,6-bis(3-vinyl-2-pyrrolidonyl)-hexane, bisacrylamides, such as methylene or ethylene bisacrylamide, bis(meth)acrylamides, such as N,N'-diethyl-1,3-bis(acrylamido)propane, 1,3-bis (methacrylamido)propane, 1,4-bis(acrylamido)butane or 1,4-bis(acryloyl)piperazine, and mixtures thereof.

8. The composition according to claim 6, wherein the at least one radically polymerizable monomer containing an acid group (c) comprises at least one monomer selected from monomers—containing a phosphoric ester group or phosphonic acid group, preferably 2-methacryloyloxyethylphenyl hydrogen phosphate, 10-methacryloyloxydecyl dihydrogen phosphate (MDP), glycerol dimethacrylate dihydrogen phosphate, dipentaerythritol pentamethacryloyloxy phosphate, 4-vinylbenzylphosphonic acid, 2-[4-(dihydroxyphosphoryl)-2-oxa-butyl]-acrylic acid and/or 2-[4-(dihydroxyphosphoryl)-2-oxa-butyl]-acrylic acid-2,4,6-trimethylphenyl ester, and/or monomers containing a carboxy group, preferably 4-(meth)acryloyloxyethyltrimellitic anhydride, 10-methacryloyloxydecylmalonic acid, N-(2-hydroxy-3-methacryloyloxypropyl)-N-phenylglycine and/or 4-vinylbenzoic acid.

9. The composition according to claim 6, wherein the one or more oligomeric carboxylic acids (d) comprises polyacrylic acid with a number average molecular mass of less than 7,200 g/mol.

10. The composition according to claim 6, wherein the one or more monofunctional monomers without acid groups (e) comprises benzyl, tetrahydrofurfuryl (meth)acrylate, isobornyl (meth)acrylate, p-cumyl phenoxyethylene glycol methacrylate (CMP-1E) and 2-([1,1'-biphenyl]-2-oxy)ethyl methacrylate (MA-836), tricyclodecane methyl (meth)acrylate, 2-(2-biphenyloxy)ethyl (meth)acrylate, 2-hydroxyethyl (methacrylate), hydroxyethylpropyl (methacrylate), 2-acetoxyethyl methacrylate, and mixtures thereof.

11. The composition according to claim 1, comprising a catalyst paste and a base paste, wherein the catalyst paste comprises a) 0.3 to 9 wt. % of at least one water-soluble sulfate and/or phosphate, b) 5 to 40 wt. % of at least one polyfunctional monomer without acid groups, c) 2 to 30 wt. % of at least one monomer containing acid groups, d) 0 to 20 wt. % of one or more oligomeric carboxylic acids, e) optionally 0.1 to 20 wt. % of one or more monofunctional monomers without acid groups, f) 25 to 80 wt. % of at least one fluoroaluminosilicate glass filler-FAS and/or radiopaque glass filler, g) optionally 1 to 50 wt. % of one or more additional fillers, h) 0.01 to 16 wt. % of at least one peroxide and/or hydroperoxide and optionally at least one photoinitiator, i) 0 to 20 wt. % of water, and j) 0.001 to 5 wt. % of one or more additives, in each case based on the total mass of the catalyst paste, and where the base paste comprises a) not applicable, b) 5 to 40 wt. % of at least one polyfunctional monomer without acid groups, c) not applicable, d) not applicable, e) optionally 0.1 to 20 wt. % of one or more monofunctional monomers without acid groups, f) 25 to 80 wt. % of at least one fluoroaluminosilicate glass filler and/or radiopaque glass filler, g) optionally 1 to 50 wt. % of one or more additional fillers, h) 0.01 to 16 wt. % of at least one suitable reducing agent and optionally a photoinitiator, i) 0 to 20 wt. % of water, and j) 0.001 to 5 wt. % of one or more additives, in each case based on the total mass of the base paste.

12. The composition of claim 11, wherein the catalyst paste and the base paste are each contained in different chambers of a dual-push syringe.

13. The composition according to claim 1 for therapeutic use as a dental material comprising a dental cement, coating material, veneering material, restorative composite, or luting cement.

14. The composition according to claim 1 for non-therapeutic use for the manufacture or repair of dental restorations comprising inlays, onlays, crowns, or bridges.

* * * * *